(12) United States Patent
Ferguson et al.

(10) Patent No.: US 7,119,339 B2
(45) Date of Patent: Oct. 10, 2006

(54) TRANSMISSION MODE TERAHERTZ COMPUTED TOMOGRAPHY

(75) Inventors: Bradley Stuart Ferguson, Northgate (AU); Shaohong Wang, Bud Lake, NJ (US); Xi-Cheng Zhang, Melrose, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 145 days.

(21) Appl. No.: 10/844,105

(22) Filed: May 12, 2004

(65) Prior Publication Data

US 2005/0023470 A1    Feb. 3, 2005

Related U.S. Application Data (63) Continuation-in-part of application No. PCT/US02/36279, filed on Nov. 13, 2002.

(51) Int. Cl.
   *G01J 5/28*    (2006.01)
   *H01L 31/00*   (2006.01)
   *G01R 31/308*  (2006.01)
   *G01N 21/17*   (2006.01)
   *G01N 21/63*   (2006.01)

(52) U.S. Cl. .............. 250/358.1; 250/332; 250/341.1; 250/341.3; 324/96

(58) Field of Classification Search .......... 250/358.1, 250/330, 332, 338.1, 339.02, 339.05, 339.06, 250/339.07, 339.08, 360.1, 370.08, 340, 250/341.1, 341.3; 324/96
See application file for complete search history.

(56) References Cited

U.S. PATENT DOCUMENTS

| | | | |
|---|---|---|---|
| 5,710,430 A | 1/1998 | Nuss | |
| 5,789,750 A | 8/1998 | Nuss | |
| 5,939,721 A | 8/1999 | Jacobsen et al. | |
| 5,952,818 A | 9/1999 | Zhang et al. | |
| 6,078,047 A | 6/2000 | Mittleman et al. | |
| 6,111,416 A * | 8/2000 | Zhang et al. | 324/96 |
| 6,414,473 B1 | 7/2002 | Zhang et al. | |
| 6,828,558 B1 * | 12/2004 | Arnone et al. | 250/341.1 |
| 6,957,099 B1 * | 10/2005 | Arnone et al. | 250/330 |
| 2001/0029436 A1 | 10/2001 | Fukasawa | |

FOREIGN PATENT DOCUMENTS

GB    2 359 619 A    8/2001

OTHER PUBLICATIONS

Zhang et al. "Terahertz Imaging Via Electrooptic Effect", IEEE Transactions on Microwave Theory and Techniques, vol. 47, No. 12 (Dec. 1999), p. 2644-2650.*

(Continued)

*Primary Examiner*—David Porta
*Assistant Examiner*—Frederick F. Rosenberger
(74) *Attorney, Agent, or Firm*—RatnerPrestia (57) ABSTRACT

A method of obtaining a series of images of a three-dimensional object by transmitting pulsed terahertz (THz) radiation through the entire object from a plurality of angles, optically detecting changes in the transmitted THz radiation using pulsed laser radiation, and constructing a plurality of imaged slices of the three-dimensional object using the detected changes in the transmitted THz radiation. The THz radiation is transmitted through the object as a scanning spot. The object is placed within the Rayleigh range of the focused THz beam and a focusing system is used to transfer the imaging plane from adjacent the object to a desired distance away from the object. A related system is also disclosed.

25 Claims, 5 Drawing Sheets

OTHER PUBLICATIONS

Recent advantages towards in-vivo THz imaging and diagnosis—Presentation by B. Ferguson, S. Wang, D. Abbott and X.-C. Zhang—International Conference on Biomedical Imaging and Sensing Applications with Terahertz Technology, Dec. 1, 2001.

X.-C. Zhang; T-Ray Computed Tomography; pp. 1-4; Hot Topic, IEEE/LEOS News Letters, 2002, USA.

Bradley Ferguson, Shaohong Wang, Doug Gray, Derek Abbot, X.-C. Zhang; T-Ray computed tomography; Optics Letters, vol. 27, No. 15, pp. 1312-1314; Aug. 1, 2002, Optical Society of America; USA.

Bradley Ferguson, Shaohong Wang, Doug Gray, Derek Abbott, X-C Zhang; Towards functional 3D T-ray imaging; Physics in Medicine and Biology; Phys. Med. Biol. 47 (2002); pp. 3735-3742; Institute of Physics Publishing; USA.

A. Boh Ruffin, Joan Decker, Laurent Sanchez-Palencia, Lenaic Le Hors, John F. Whitaker, Theodore B. Norris, J. V. Rudd; Time reversal and object reconstruction with single-cycle pulses; Optic Letters, vol. 26, No. 10; pp. 681-683; May 15, 2001; Optical Society of America; USA.

Zhiping Jiang, X.-C. Zhang; THz Imaging via Electro-Optic Effect; 1999 IEEE MTT-S Digest, pp. 941-944; IEEE; USA.

Peter M. Van Den Berg, Ralph E. Kleinman; A contrast source inversion method; Inverse Problems 13 (1997); pp. 1607-1620; IOP Publishing Ltd., UK.

Frank Natterer, Frank Wubbeling; Chapter 3.3: Diffraction Tomography, pp. 46-50; Chapter 5: Reconstruction Algorithms, pp. 81-83; Mathematical Methods in Image Reconstruction; USA.

Zhiping Jiang, X. G. Xu, X.-C. Zhang; Improvement of terahertz imaging with a dynamic subtration technique; Applied Optics, vol. 39, No. 17, Jun. 10, 2000; pp. 2982-2987; Optical Society of America; USA.

Q. Wu, T.D. Hewitt, X.-C. Zhang; Two-dimensional electro-optic imaging of THz beams; Appl. Phys. Lett 69 (8), Aug. 19, 1996; pp. 1026-1028; American Institute of Physics; USA.

F.G. Sun, Zhiping Jiang, X.-C. Zhang; Analysis of terahertz pulse measurement with a chirped probe beam; Applied Physics Letters, vol. 73, No. 16, Oct. 19, 1998; pp. 2233-2235; American Institute of Physics; USA.

Zhiping Jiang, X.-C. Zhang; Electro-optic measurement of THz field pulses with a chirped optical beam; Applied Physics Letters, vol. 72, No. 16, Apr. 20, 1998; pp. 1945-1947; American Institute of Physics; USA.

Z. G. Lu, P. Campbell, X.-C. Zhang; Free-space electro-optic sampling with a high-repetition-rate regenerative amplified laser; Appl. Phys. Lett. 71 (5), Aug. 4, 1997; pp. 593-595; American Institute of Physics; USA.

Daniel M. Mittleman, Stefan Hunsche, Luc Boivin, Martin C. Nuss; T-ray tomography; Optic Letters, vol. 22, No. 12; Jun. 15, 1997; pp. 904-906.

Bradley Ferguson, Shaohong Wang, Douglas A. Gray, Derek Abbott, XI-Cheng Zhang; Terahertz Imaging of biological tissue using a chirped probe pulse; Electronics and Structures for MEMS II; Proceedings of SPIE, vol. 4591; Nov. 2001; pp. 172-184.

A.C. Kak and Malcolm Slaney; Principles of Computerized Tomographic Imaging; Society of Industrial and Applied Mathematics; 2001; pp. 17-25.

Martin C. Nuss; Chemistry Is Right for T-Ray Imaging; IEEE Circuits & Devices; Mar. 1996; pp. 25-30.

Shiping Jiang and X.-C. Zhang, 2D Measurement and Spatio-Temporal Coupling of Few-Cycle THz Pulses; Optics Express, vol. 5, No. 11, Nov. 22, 1999, pp. 243-248.

* cited by examiner

TRANSMISSION MODE TERAHERTZ COMPUTED TOMOGRAPHY

This application is a continuation-in-part application of PCT International Application Number PCT US02/36279 filed on Nov. 13, 2002 designating the United States, the entire contents of which are incorporated in this document by reference.

The U.S. Government has a paid-up license in this invention and the right in limited circumstances to require the patent owner to license others on reasonable terms as provided for by the terms of Contract No. DE-FG07-98ER6270 awarded by the Department of Energy and Contract Nos. DAAD-19-99-1-0333 and DAAD-1999C0045 awarded by the U.S. Army.

FIELD OF THE INVENTION

The invention relates generally to terahertz time domain spectroscopy (THz-TDS) and, more particularly, to systems and associated methods for high resolution terahertz computed tomography (THz-CT).

BACKGROUND OF THE INVENTION

The term "terahertz" (THz), originally used by sub-millimeter spectroscopists to describe spectral lines with frequencies in the trillions of hertz, today is applied to broadband pulsed electromagnetic (EM) radiation between the infrared and microwave bands of the EM spectrum, ranging from 0.1 to 10 THz. The photon energies of THz radiation range from 0.4 to 80 mev, which corresponds to the range of fundamental energies associated with changes between molecular energy levels.

Over the past 20 years the technologies in the THz field have developed significantly, both in the generation of THz radiation as well as in its detection. Recent advances in high-speed optoelectronic and femtosecond laser technology facilitate generation and detection of short bursts of terahertz radiation, which has proven to be extremely useful for spectroscopic measurements in the sub-millimeter-wave range. Terahertz imaging combines these coherent spectroscopic measurements with real-time imaging and advanced signal processing and recognition, so that each pixel element of the image contains spectroscopic information about the object. Terahertz radiation is described in greater detail in an article by M. Nuss entitled "Chemistry is Right for T-Ray Imaging," Circuits & Devices, IEEE (March, 1996).

Typical apparatus and associated imaging methods for free-space electro-optic characterization of propagating terahertz beams are described in U.S. Pat. No. 5,952,818 issued on Sep. 14, 1999 to Zhang et al. and assigned to the assignee of the present invention, Rensselaer Polytechnic Institute. The sensing technique is based on a non-linear coupling between a low-frequency electric field (terahertz pulse) and a laser beam (optical pulse) in an electro-optic crystal, such as a zinc telluride (ZnTe) crystal. Modulating the crystal's birefringence by applying the polarized electric field to the crystal modulates the polarization states of an optical probe beam passing through the crystal. This ellipticity modulation of the optical beam is then polarization-analyzed to provide information on both the amplitude and phase of the applied electric field.

A further improvement in terahertz imaging is disclosed in U.S. Pat. No. 6,414,473 issued on Jul. 2, 2002 to Zhang et al. and also assigned to Rensselaer Polytechnic Institute. The described imaging system in this reference employs a chirped optical beam and dynamic subtraction to rapidly reconstruct an image, thereby providing a system that is suitable for real-time imaging applications. According to this patent, the imaging system generates a free-space electromagnetic radiation pulse positionable to pass through the object to be imaged. One of an electro-optic crystal or a magneto-optic crystal is positioned so that the electromagnetic radiation pulse passes through the crystal after passing through the object.

The system further generates a chirped optical probe signal to impinge the crystal simultaneously with the electromagnetic radiation pulse passing through the crystal so that a temporal waveform of the radiation is encoded onto a wavelength spectrum of the chirped optical probe signal. The chirped optical probe signal modulated by the free-space radiation is then passed to a decoder for decoding a characteristic of the free-space electromagnetic radiation using the chirped optical probe signal with the temporal waveform of the radiation encoded on the signal. The system further determines a characteristic of the object using the characterization of the free-space electromagnetic radiation pulse after passing through the object.

Both of the patents summarized above are incorporated, in their entirety, in this document by reference.

Tomography refers to the cross-sectional imaging of an object from measuring either the transmitted or reflected illumination. Three-dimensional THz tomography coupled with spectroscopic analysis has many potential applications such as mail package examination, security screening, and nondestructive inspection. In 1997, Mittleman et al. demonstrated THz tomography in which the 3D image of a floppy disk was successfully reconstructed using reflected THz pulses and a digital processing algorithm. A number of assumptions were made in the use of the algorithm: first that the targets had no dispersion and diffraction, second that the reflection is so weak that multiple reflections could be ignored, and third that the refractive index is uniform in each layer examined. Such assumptions restrict the applicability of the tomographic technique and exclude the possibility of spectroscopic analysis.

Although computed tomography is well known in X-ray radiographic imaging, a serious problem in reconstructing an image using THz computed tomography is that the THz wave does not satisfy the short wave limit as the X-ray satisfies in X-ray computed tomography. For example, if one attempts to image a 10 cm target using a THz beam with a 10 cm Rayleigh range, the minimum THz beam size will have an electric field waist of 6 mm. Therefore, if one treats the beam as a ray line, the resolution will not be any better than 6 mm. This implies that the resulting image of the target only contains 30×30 pixels—an inadequate resolution. Therefore, a need remains for a THZ CT imaging system and imaging method that provide improved resolution compared with the resolution obtained using traditional X-ray computed tomography technology and that permit the use of the computed tomographic algorithm.

SUMMARY OF THE INVENTION

In its broader aspect, the invention includes a method of obtaining a series of images of a three-dimensional object by transmitting pulsed, focused terahertz (THz) radiation through the entire object from a plurality of angles; optically detecting changes in the transmitted THz radiation using pulsed laser radiation; and constructing a plurality of imaged slices of the three-dimensional object using the detected changes in the transmitted THz radiation. According to this invention, there is, therefore, provided a THz imaging method for performing computed tomography using THz frequency radiation in which the method has the following steps.

I. A reference signal is obtained upon execution of three sub-steps.

A. First, pulsed THz radiation is transmitted through a path that includes a sample holding area and the pulsed THz radiation is impinged onto a sensor. The pulsed radiation beam is focused with a focusing system including a focusing element having a diameter smaller than the distance measured from the focusing element to the sample area, the sample area is smaller than the Rayleigh range of the focused THz beam, and the focusing system is designed to focus a plane adjacent the sample area onto the sensor.

B. Next, a pulsed optical radiation probe beam having a first amplitude is transmitted through a sensor when the sensor is illuminated with THz frequency electromagnetic radiation.

C. Third, a second amplitude of the optical pulse is detected after the optical pulse has passed through the sensor.

II. A sample is placed in the sample holding area.

III. A pulsed THz radiation beam is transmitted through an area of the sample representing a pixel.

IV. The pulsed THz radiation beam following transmission through the sample is impinged onto the sensor while transmitting the optical probe beam through the sensor.

V. Again, the amplitude of the probe beam emerging from the sensor is detected.

VI. Steps III–V are repeated a plurality of times while changing the relative time of arrival of the optical probe beam pulse and THz radiation pulse on the sensor to obtain a temporal profile of the THz pulse.

VII. A calculation is made of the frequency domain of THz amplitude and frequency.

VIII. Steps III–VII are repeated a plurality of times for a plurality of sample pixel areas and for a plurality of sample orientations relative to the THz beam to obtain the composite frequency domain for a plurality of pixels from a plurality of angles.

IX. An image of the sample is reconstructed from the composite frequency domain.

Another aspect of the invention includes an apparatus for performing coherent Terahertz wave computed tomography, the apparatus having:

i. a sensor for modulating the amplitude of incident optical radiation as a result of illuminating the sensor with THz frequency electromagnetic radiation;

ii. a probe beam comprising pulsed optical radiation directed onto the sensor along a first path and exiting the sensor along a second path;

iii. a pulsed THz radiation beam directed onto the sensor through a third path comprising:
  a. a sample area,
  b. a THz radiation beam focusing system comprising at least one focusing element having a diameter,
  c. a support for holding a sample in the sample area at a first orientation relative to a propagation direction of the pulsed THz radiation beam, and
  d. a mechanism for altering the first orientation; and iv. a detector in the second path for detecting the amplitude of the pulsed optical radiation beam;

wherein:
1. preferably the focusing element diameter is smaller than a distance measured from the focusing element to the sample area;
2. the sample area is smaller than the Rayleigh range of the THz beam; and
3. the focusing system is designed to focus a plane adjacent the sample area onto the sensor.

The detector detects the signal amplitude for individual pixels of the object for each orientation and the apparatus also comprises a mechanism for constructing a three-dimensional image of the object using the information obtained for the plurality of pixels for the plurality of orientations.

Accordingly, in one embodiment, the apparatus may include a mechanism for rotating the object relative to the THz pulse about a z-axis of the object to obtain a plurality of projection angles. In such an embodiment, the object may be physically rotated or the source for providing the THz pulse may be physically rotated.

In one embodiment, the apparatus comprises a mechanism for providing a chirped optical probe pulse, and the mechanism for detecting the modulated optical probe pulse comprises a spectrometer and a charged coupled device (CCD) camera. In another embodiment, the apparatus further comprises a delay stage for providing a plurality of delays between the THz pulse and the optical probe pulse, and the detector is a photosensitive element or a photoconductive antenna.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The invention will next be described with reference to the figures in which the same numbers are used to indicate the same elements in all figures. The figures are used to illustrate the invention and avoid elements not needed to explain the invention, so as not to unduly clutter and complicate the illustrations.

Computed tomography is conceptually similar to X-ray tomography in that both imaging processes obtain imaging data as data representing a series of individual slices taken through an object. As mentioned above, however, although CT imaging is well known in X-ray radiography, the wave differences between X-ray radiation and THz radiation are sufficiently significant so that X-ray CT technology may not be simply applied to THZ-CT applications. The present invention overcomes the limitations due to the wave differences between THz radiation and X-ray radiation and describes a practical THz-CT system that successfully uses X-ray CT algorithms for image capture and reconstruction.

Figure 1:
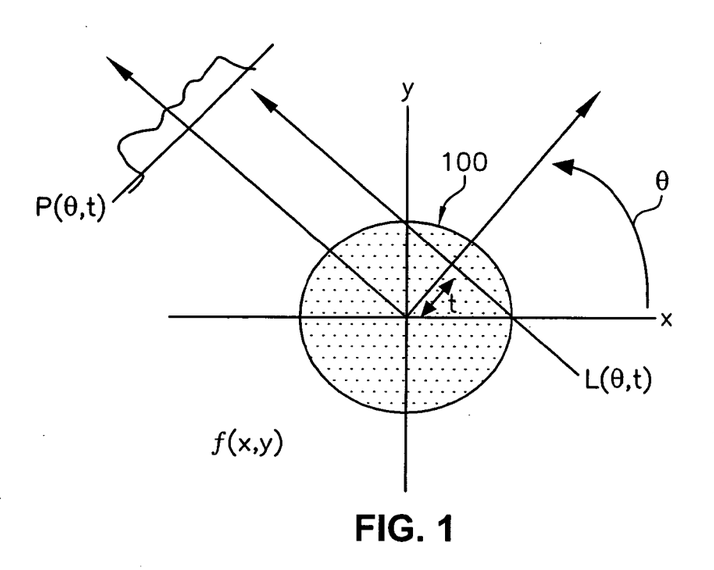
FIG. 1 is a schematic representation of the relative positions of a sample and the THz radiation and associated detector for examining the sample in accordance with this invention.

FIG. 1 illustrates the fundamental concept of THz CT. A sample 100 (the object) is scanned with THz radiation in the x-y plane in the direction of line L. When a T-ray is propagated through the sample, its attenuation, or object projection $P(\theta,t)$, is the line integral of the object function $f(x,y)$ along the line L, which is determined by the line orientation angle, $\theta$, and the offset, t, from the object origin. is The object projection can be obtained by measuring the signal at various $\theta$ and t via rotating the sample. In the alternative, the radiation source and detector may be rotated while the sample remains stationary. This process is repeated to generate imaging data (including a temporal THz profile) for a number of projection angles $\theta$.

Figure 2:
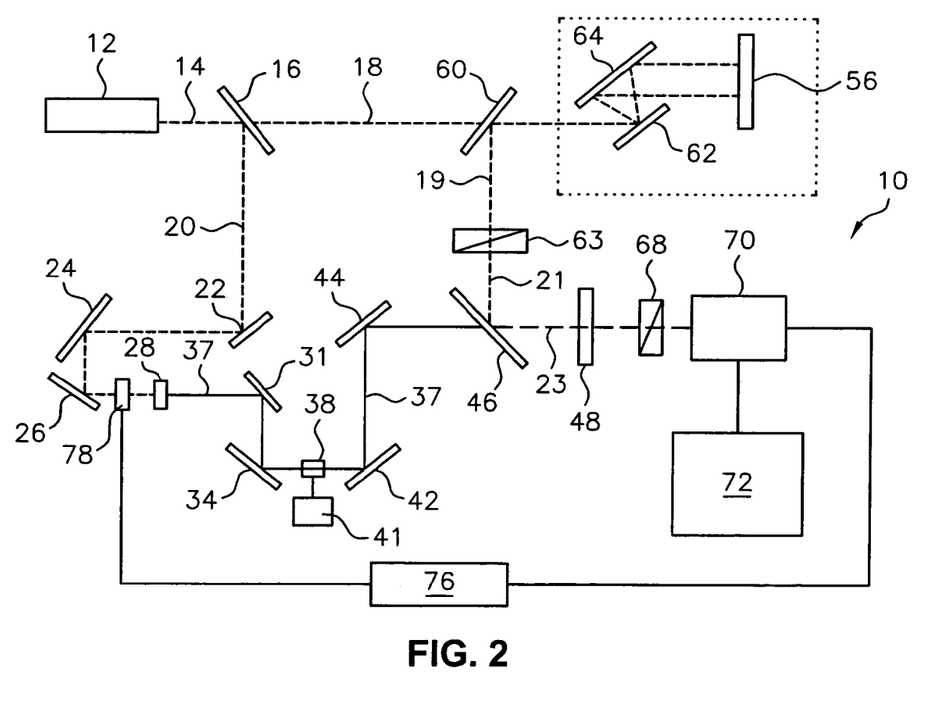
FIG. 2 is a schematic representation of a system useful in implementing THz-CT in accordance with this invention.

FIG. 2 shows a THz imaging system 10 constructed in accordance with this invention. As shown in FIG. 2, there is provided a femtosecond laser 12 emitting a pulsed optical beam 14. Beam 14 is split using a pellicle 16 into a pulsed pump beam 20 and a pulsed probe beam 18. The pump beam 20 is directed through a variable delay path formed by reflectors 22, 24, and 26 onto a THz generator radiation emitter 28. Emitter 28 produces a pulsed THz beam 37, in effect converting the incident laser pulsed beam into a THz pulsed beam.

The pulsed THz beam 37 emitted by the THz emitter 28 is reflected by a reflector 31 and focused with a parabolic mirror 34 onto the sample 38. The sample 38 is positioned in the THz beam path on a sample holding stage 41 which is preferably adapted to provide rotation and translation of the sample 38 as needed to accomplish scanning of the sample 38 with the THz beam 37. Following transmission through the sample 38, the THz beam 37 is directed onto a sensor 48 comprising an electro-optic (EO) crystal, preferably using a set of parabolic mirrors 42 and 44 to project the focused THz beam 37 onto sensor 48 as will be discussed in more detail below.

Figure 3:
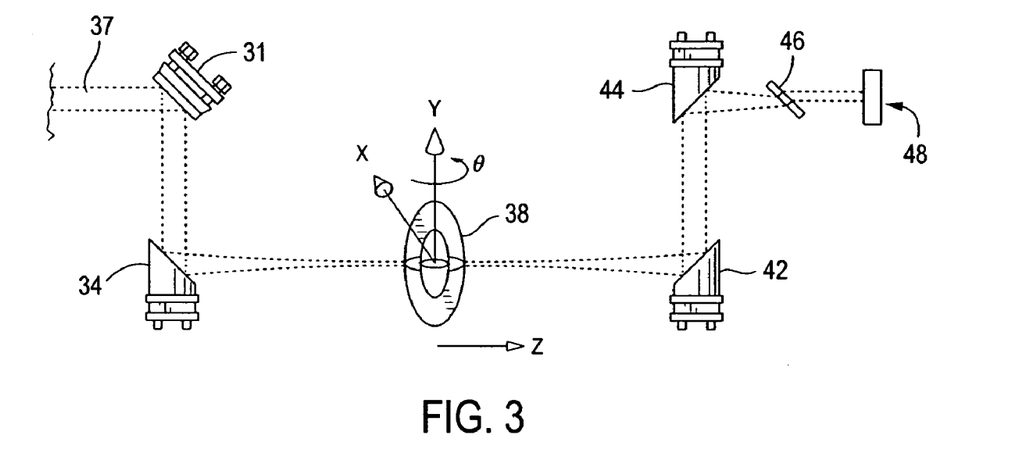
FIG. 3 illustrates a portion of the system shown in FIG. 2 including the THz beam focusing set up relative to a target object, and two parabolic mirrors used to form an equivalent thin lens for removing the detection plane from a position adjacent the target to a position removed from the target.

FIG. 3 shows the focusing system in more detail. The incoming THz beam 37 is shown reflected off the reflector 31 and focused by the parabolic mirror 34 to a spot onto the sample 38. Following passage through the sample 38, a system of the two parabolic mirrors 42 and 44 and the pellicle 46 project an image of the focused THz spot onto the sensor 48. Also shown in FIG. 3 is a Cartesian x-y-z coordinate system illustrating the positioning of the sample 38 relative to the THz beam 37 propagation and the rotational angle $\theta$.

The two parabolic mirrors 42 and 44 correspond to an equivalent thin lens with an effective focal length f given by $$1/f = 1/f_1 + 1/f_2,$$

where $f_1$ is the focal length of the parabolic mirror 42 and $f_2$ is the focal length of the parabolic mirror 44.

Figure 4:
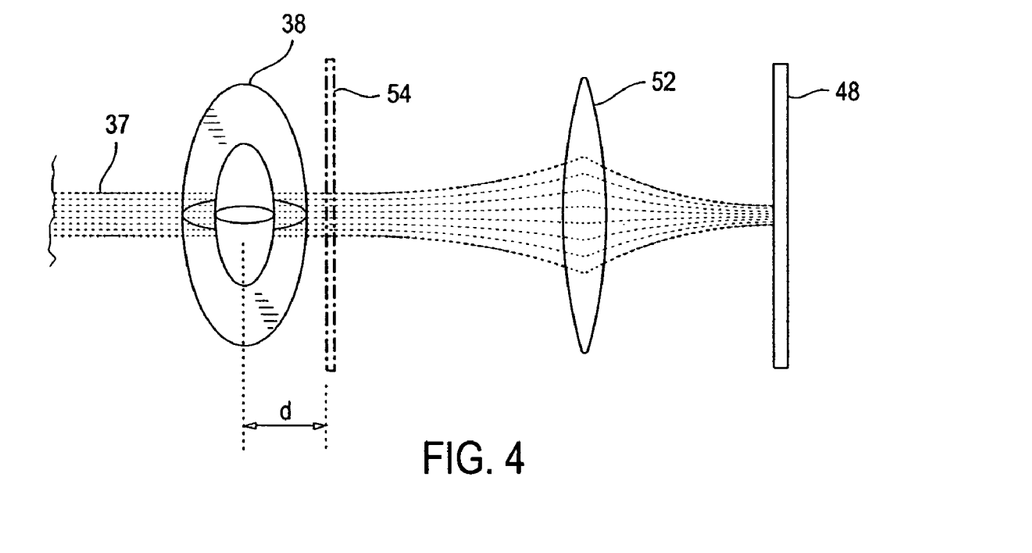
FIG. 4 illustrates the relative positions of the equivalent thin lens, the focused THz beam, the detection plane, and the sensor for a system built in accordance with the present invention.

Referring next to FIG. 4, there is shown the details of the focused THz beam 37 in relation to the sample 38, and the equivalent thin lens 52 formed by the two mirrors 42 and 44. The sample 38 is shown positioned fully within the Rayleigh range of the focused incident THz beam 37 focused by parabolic mirror 34 (not shown in FIG. 4). Preferably, the diameter of the focusing element is also selected to be much smaller than the distance measured from the focusing element to the sample area. This design selection requires, in turn, that the numerical aperture (N.A.) of the equivalent thin 52 is less than about 0.173.

In order to apply X-ray CT algorithms in image reconstruction, the radiation beam exiting from the sample 38 is detected at a detection plane 54 adjacent the sample 38 at a distance "d" from the center of the target along the z-axis such that the beam diffraction angle is within about 5 degrees.

When the target is fully within the Rayleigh zone and the detection plane 54 also within the same zone or no further than the point where the beam diffraction angle is within about 5 degrees, the THz beam in the target space can be and is treated as a planar THz wave. Satisfying this condition permits using the same imaging reconstruction techniques and algorithm solutions as used for X-ray CT, as more fully explained in chapters 2 and 4 of a Thesis by Dr. Shaohong Wang entitled "Three-Dimensional Terahertz Imaging," dated July 2003, and located at the Rensselaer Polytechnic Institute library in Troy, N.Y. U.S.A. Copies of the most pertinent pages are attached to this document as Appendices A and B.

In a typical arrangement for THz CT imaging, the Rayleigh range of the focused THz beam in the target space may be equal to 5 cm., in which case a 4 cm sample may be easily imaged because the Rayleigh range of THz beam is larger than the size of the target. For a THz wave with a wavelength of 0.3 mm, however, the distance "d" would be on the order of about 10 mm. Obviously, this dimension is an impractical location to position the sensor. The solution to this problem is to use a thin lens 52 to transfer the detection plane 54 from its position adjacent the sample to a more distant location. The two parabolic mirrors which form a thin lens equivalent as discussed above are a preferred way, therefore, to accomplish this transfer, and actual radiation detection is done at a convenient distance from the sample.

Returning next to FIG. 2, optical pulse probe beam 18 is directed through a pellicle 60 along the path 19 through a first polarizer 63 to generate a purely linearly polarized optical pulsed probe beam 21. The polarized optical probe beam 21 is reflected by pellicle 46 and propagates co-linearly with the THz beam 37 along the path 23 so that both the optical and the THz radiation pulses impinge on sensor 48. There are several different types of THz sensors, a commonly used one being a ZnTe crystal. Sensor 48 modulates the polarization of the linearly polarized optical probe beam 21 which becomes slightly elliptical. A second polarizer 68 is used to convert the polarization modulation into an intensity modulation. This second polarizer 68 has a polarization axis that is perpendicular to the polarization axis of the first polarizer 63.

The polarized optical pulsed probe beam 21 arrives at the THz sensor 48 at the same time as the start of the THz pulse and allows the instantaneous THz electric field to be measured. The birefringence of this crystal is dependent upon the incident electric field. The THz field changes the birefringence of the crystal. A birefringent crystal rotates the polarization of an optical beam that is transmitted through it. Therefore, the stronger the incident THz field, the more the probe beam polarization is rotated.

The polarization of the probe beam can be measured by passing it through the linear second polarizer 68. The amplitude of the probe beam after the polarizer is dependent upon its polarization, which in turn is dependent upon the THz field amplitude. The amplitude of the THz pulse may be measured using a detector 70, which typically may comprise a photodiode, coupled to a computer 72. This detection technique is referred to as free-space electro-optic sampling (FSEOS).

Because the optical probe beam and the THz pulse propagate through the ZnTe crystal at the same velocity, the optical signal-exiting the sensor 48 represents the instantaneous THz field at the instant the probe pulse reaches the THz detector.

As shown in FIG. 2, the pump beam 20 is reflected by a group of mirrors such as reflectors 22, 24, and 26. By mounting the mirrors on a translation stage, the path length of the pump beam can be modified. If the pump beam path is shortened, the THz pulse will reach the THz detector slightly before the optical probe beam pulse. The probe beam pulse will then measure the THz field at a slightly later time. By repeating this process a plurality of times, the THz pulse temporal profile is measured. This time domain THz pulse may be used to calculate numerically, via Fourier transform, the frequency domain THz amplitude and phase.

A "reference" signal is also similarly measured by removing the sample from the sample stage and measuring the THz pulse in the manner described above. By comparing the THz pulses measured with and without the sample in the system, the phase and amplitude changes caused by the sample can be determined.

To obtain the data required for T-ray CT image reconstruction, the THz pulse measurement procedure described above is repeated while the sample target is raster scanned through the THz focal point. The THz pulse is measured for each "pixel" of the target to obtain a THz "image." The target is then rotated and the THz "image" is measured for multiple projection angles to provide a complete set of data for 3D image reconstruction of the target using well-known filtered back-projection techniques. The amplitude or phase of the THz pulses at any frequency may be used to develop a number of different 3D images.

The need to obtain a plurality (hundreds) of temporally displaced pulse data for each pixel for each angular exposure of a target through individual exposures may be obviated through a preferred embodiment using a chirped optical pulse technique to obtain the complete time domain data per pixel in one exposure.

Again referring to FIG. 2, there is also shown a grating pair 62, 64 for chirping and stretching the optical probe beam 18 prior to directing the optical pulse along path 19. The probe beam is frequency chirped and temporally stretched by grating pair 62, 64 by passing probe beam 18 through the pellicle 60 to the grating pair for reflection off a mirror 56. The linearly chirped pulse is equivalent to a series of sub-pulses that have different wavelengths and are temporally delayed. Due to the negative chirp of the grating (pulse with decreasing frequency versus time), the blue component of the pulse leads the red component.

The chirped probe signal is returned from grating pair 62, 64 to the reflective surface of the pellicle 60 and passed through the first polarizer 63 to generate a purely linearly polarized optical pulsed probe beam 21 as discussed previously. When the chirped probe beam and a THz pulse co-propagate in the electro-optic crystal, different portions of the THz pulse, through Pockels effect, modulate the different wavelength components of the chirped pulse. Therefore, the THz waveform is encoded onto the wavelength spectrum of the probe beam.

In such embodiment, detector 70, which in the previous embodiment comprises a single photodiode, is replaced by a spectrometer, e.g., comprising a grating and lens combination coupled to a detector array (LDA or CCD), and the detector array is used to measure the spectral distribution of the modulated chirped optical beam. The spectrometer spatially separates the different wavelength components and thus reveals the temporal THz pulse. The spatial signal output from the spectrometer is then measured using, for example, a CCD.

Computer 72 is used to process and store the retrieved data. The temporal THz signal can be extracted by again measuring the difference between the spectral distributions of the probe pulse with and without THz pulse modulation applied via the electro-optic crystal or sensor 48, as is known in the art and described in detail in U.S. Pat. No. 6,414,473.

The mathematical field of inverse problems for 3D image reconstruction is very well established and a large number of potential algorithms exist in reconstructing the THz data. For example, the filtered back-projection algorithm may be used to perform the inverse Radon equation to reconstruct the sample. See, for example, A. Kak & M. Slaney, "Principles of Computerized Tomographic Imaging," Society of Industrial and Applied Mathematics, 2001. See also the aforementioned thesis by Dr. Shaohong Wang.

This reconstruction algorithm is performed to reconstruct a number of features from the measured data depending on the desired application. The amplitude of the THz pulse and the timing of the peak of the pulse are prime examples. The reconstructed amplitude image gives a 3D image dependent on the bulk absorption of the sample in the far-infrared (including Fresnel losses) while the reconstructed timing image provides a refractive index map of the sample in 3D.

Full reconstruction algorithms use the Fourier transform of the obtained data to reconstruct the frequency-dependent refractive index and absorption coefficient for every voxel in the three-dimensional sample space. This spectral information may then be used to identify different materials within the target.

When using the embodiment employing the chirped optical pulse probe, the steps of obtaining the stored information are repeated for a plurality of x and y locations relative to the object and for a plurality of projection angles relative to the object. Such projection angles may collectively represent a full or partial revolution of the object, for example a 180 degree or 360 degree revolution, but lesser revolutions may also be used. Then, a plurality of two-dimensional tomographic slices of the object may be constructed from the collected and stored information using any algorithm known in the art, such as but not limited to a filtered back-projection algorithm as discussed earlier.

A three-dimensional image of the object may then further be constructed from the two-dimensional slices. Numerous techniques of data processing can next be borrowed from X-ray technology to create three-dimensional virtual images of the object, sections, and flight through internal portions as is well known in the art.

In yet another embodiment, dynamic signal subtraction may be employed if desired. If dynamic signal subtraction is used, a synchronization signal is provided by synchronizer 76 between the THz emitter 28 and the pulse detector 70 using a frequency divider and an EO modulator 78 (see FIG. 2) such that the pulse rate of the pump beam incident on the THz emitter is one half the scanning frequency of the CCD detector. Dynamic subtraction techniques and their use in improving terahertz imaging are fully described in an article entitled "Improvement of terahertz imaging with a dynamic subtraction technique," by Z. Jiang, X. Xu, and X. Zhang published in Applied Optics, Vol. 39, No 17, 10 June 2000, pp. 2982–2987. This article is incorporated in this document by reference in its entirety.

Dynamic subtraction is optional, and is simply one way of improving signal-to-noise ratio or SNR. Other methods of improving SNR include increasing the THz power by using a different source or a higher THz antenna bias, for example, or increasing the CCD acquisition or averaging time. Increasing the CCD acquisition or averaging time, however, has the disadvantage of slowing the imaging speed.

The Fourier Slice Theorem is then used together with interpolation or back-propagation techniques to solve for the object function, f, as is known in the art. These techniques are described in more detail by Kak & Slaney in "Principles of Computerized Tomographic Imaging," Society of Industrial and Applied Mathematics, 2001, incorporated in this document by reference.

The system may include a mechanism for rotating the object relative to the THz pulse about a z-axis of the object to obtain the plurality of projection angles. In such an embodiment, the object may be physically rotated or the source of the THz pulse and the detector may be physically rotated relative to the sample. In another embodiment, the THz pulse may be transmitted from a plurality of projection angles simultaneously, with a corresponding detector provided for each of the projection angles.

Figure 5:
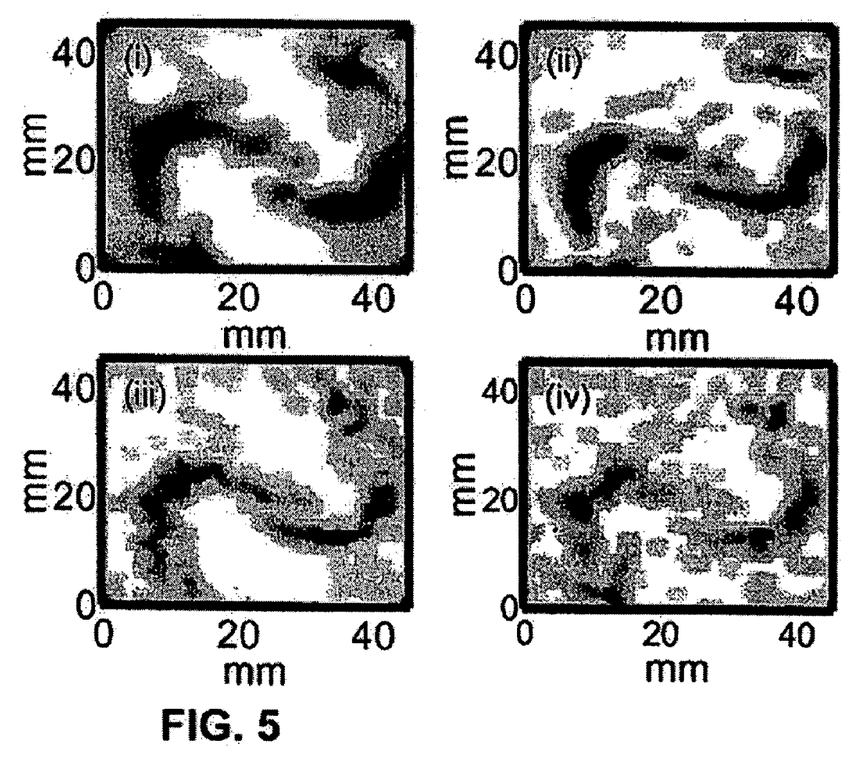
FIG. 5 shows an image of an "S"-shaped piece of polyethylene film obtained in accordance with the present invention.

FIG. 5 shows a piece of polyethylene film bent into an "S"-shaped curve placed on stage 41 of the system 10 illustrated in FIG. 2 together with four reconstructed cross sections. These sections were created by applying to the captured data the Fourier transform and applying the filtered back-projection algorithm to the imaginary part of the Fourier domain coefficients at four different frequencies. The frequencies corresponding to each of the cross sections, beginning with the top left and moving clockwise, are: (i) 0.2 THz, (ii) 0.4 THz, (iii) 0.6 THz, and (iv) 0.8 THz.

Figure 6:
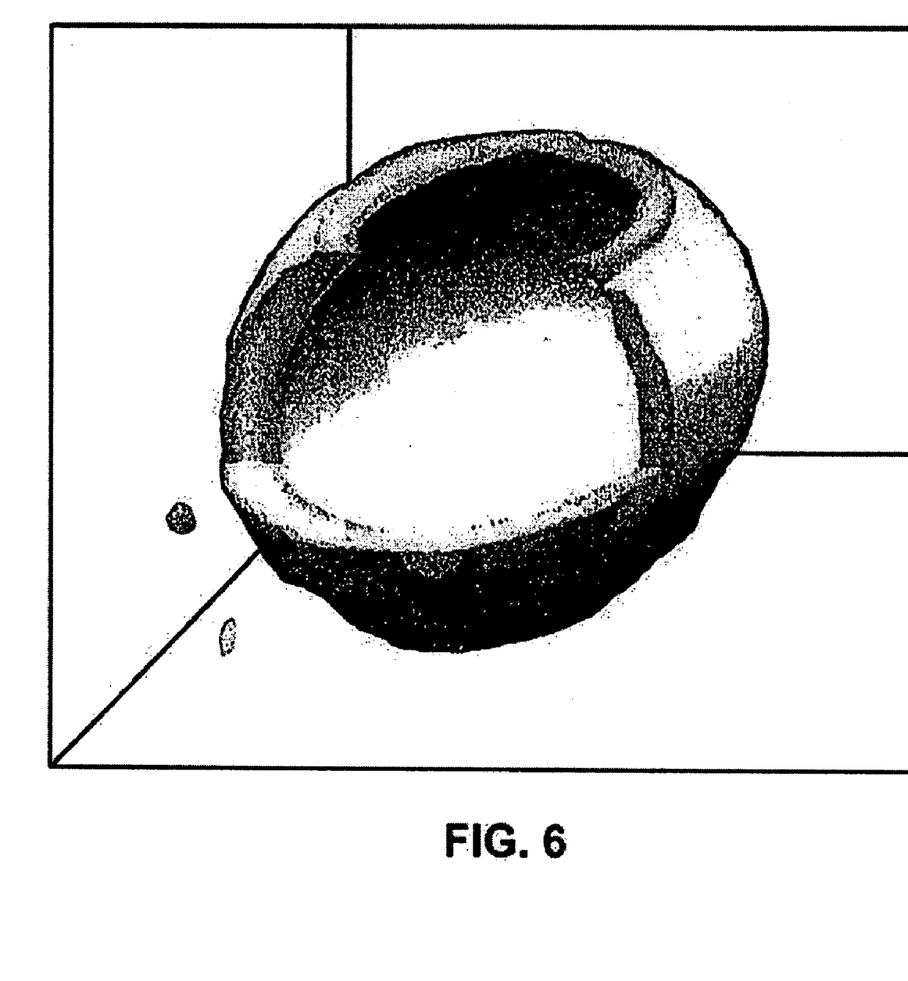
FIG. 6 shows an image of a table tennis ball obtained according to this invention.

FIG. 6 shows the reconstructed image of a table tennis ball imaged by scanning the ball with THz radiation in accordance with the present invention using the system illustrated in FIG. 2. Part of the data has been cut away to allow the interior of the ball to be viewed.

Figure 7:
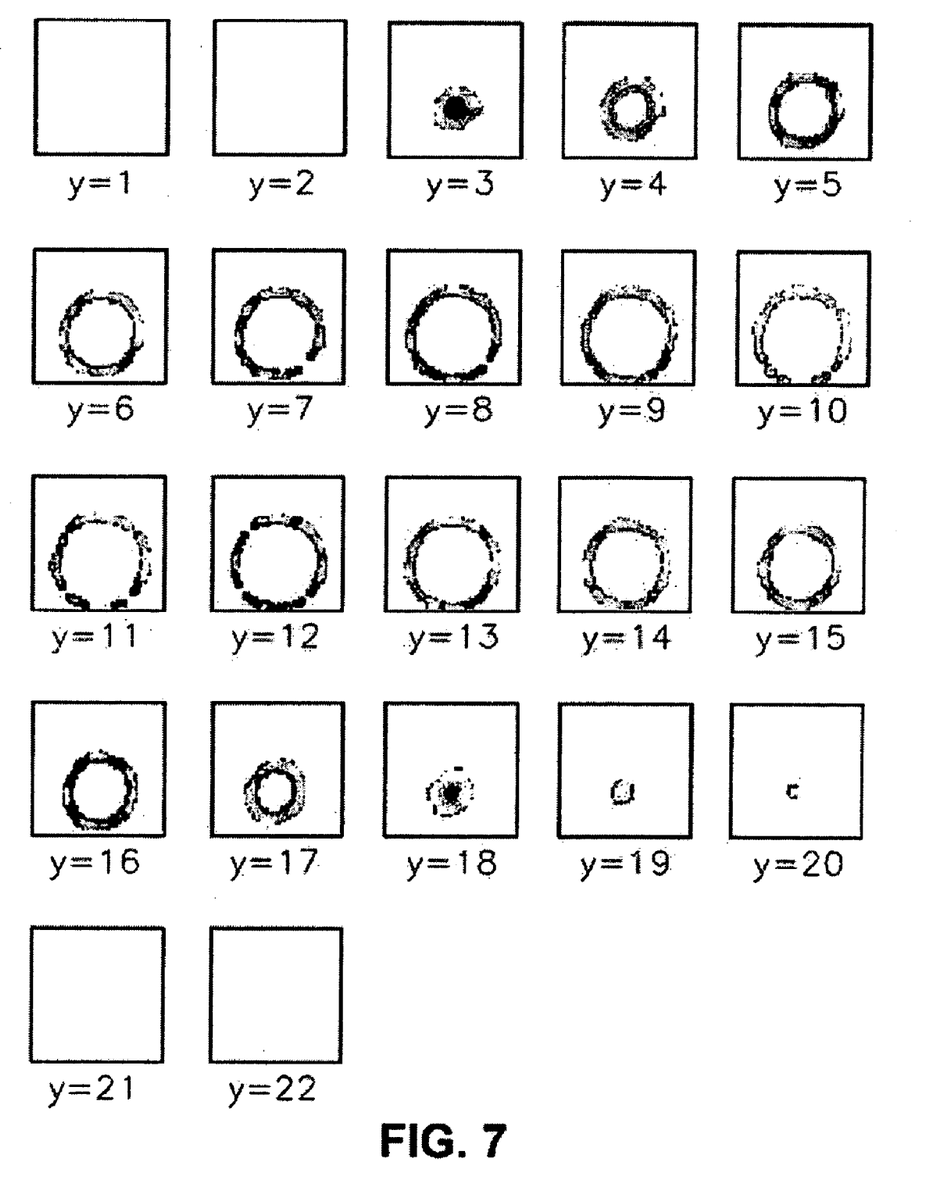
FIG. 7 shows a plurality of tomographic slices taken across the table tennis ball shown in FIG. 6 reconstructed with one of the methods according to the present invention.

FIG. 7 shows a series of tomographic-type slices representing a reconstruction of the tennis ball using the timing of the peak of the pulse estimated with sub-pixel accuracy. Alternatively, a similar reconstruction may be obtained using the peak of the THz pulses as the input to the filtered back-projection algorithm.

The terahertz radiation exposure and detection method described above may be used to identify specific materials by detecting the change in the radiation as a function of the frequency of the radiation, because such change depends on the dielectric constant of the irradiated material. Such information is obtained using spectroscopic detection of the THz pulse in detecting the changes in the electromagnetic radiation for each of the plurality of exposure angles.

Biomedical diagnosis is another area where the submillimeter spectroscopic measurements obtained through THz radiation exposure systems in accordance with the present invention have applications as they provide a wealth of information about the sample under test. Such technology is described in detail in an article entitled "Terahertz imaging of biological tissue using a chirped probe pulse," in Electronics and Structures for MEMS II, N. Bergmann, Editor, Proceedings of SPIE, Vol. 4591, pp. 172–184 (2001), the contents of which are fully incorporated by reference in this document.

Although the invention is illustrated and described above with reference to specific embodiments, the invention is not intended to be limited to the details shown. Rather, various modifications may be made in the details within the scope and range of equivalents of the claims and without departing from the invention. For example, methods using optical pulses other than chirped optical pulses may be used, as are known in the art. Furthermore, the method is not limited to use only with EO crystals. For example, photoconductive dipole antenna (PDA) detection may also be used.

What is claimed is:

1. An apparatus for performing coherent terahertz (THz) wave computed tomography, the apparatus comprising:
   i. a sensor for modulating an amplitude of incident optical radiation as a result of illuminating the sensor with THz-frequency electromagnetic radiation;
   ii. means for generating a probe beam, said probe beam including pulsed optical radiation directed onto the sensor along a first path and exiting the sensor along a second path and;
   iii. means for generating a pulsed THz radiation beam directed onto the sensor through a third path wherein said third path includes:
      a. a sample area,
      b. a THz radiation beam focusing system having at least one focusing element with a diameter,
      c. a support for holding a sample in the sample area at a first orientation relative to a propagation direction of the pulsed THz radiation beam, and
      d. means for altering the first orientation; and
   iv. a detector in the second path for detecting the amplitude of the pulsed optical radiation beam;
   wherein:
      a. the sample area is smaller than the Rayleigh range of the THz beam; and
      b. the focusing system is designed to focus an imaging plane adjacent the sample area onto the sensor.

2. The apparatus according to claim 1 wherein the focusing element diameter is smaller than a distance measured from the focusing element to the sample area.

3. The apparatus according to claim 2 wherein the means for altering the first orientation includes means for translating and for rotating the sample relative to the propagation direction of the THz radiation pulse.

4. The apparatus according to claim 2 wherein the means for altering the first orientation includes means for altering the propagation direction of the THz radiation pulse.

5. The apparatus according to claim 2 wherein the focusing system designed to focus a plane adjacent the sample area onto the sensor has a pair of parabolic reflectors.

6. The apparatus according to claim 2 further comprising a THz pulse delay stage having two moveable reflectors.

7. The apparatus according to claim 2 further comprising means for chirping the optical probe pulsed radiation beam prior to impinging the beam onto the sensor.

8. The apparatus according to claim 7 wherein said detector comprises a spectrometer.

9. The apparatus according to claim 8 wherein the detector comprises a CCD array.

10. The apparatus according to claim 9 further comprising a synchronization signal generator providing a synchronization signal for synchronizing and regulating a scanning frequency of the CCD array and a pulse rate of the THz pulse.

11. The apparatus according to claim 2 wherein the imaging plane is within the Rayleigh range of the THz beam.

12. The apparatus according to claim 1 wherein the imaging plane is within the Rayleigh range of the THz beam.

13. A method for performing computed tomography using THz-frequency radiation, the method comprising:
   I. obtaining a reference signal by:
      i. transmitting pulsed THz radiation through a path that includes a sample holding area and a focusing system and impinging the pulsed THz radiation onto a sensor, wherein the sample holding area is smaller than a Rayleigh range of a focused THz beam and the focusing system is designed to focus a plane adjacent the sample holding area onto the sensor;
      ii. transmitting a pulsed optical radiation probe beam having a first amplitude through the sensor when the sensor is illuminated with THz-frequency electromagnetic radiation, and
      iii. detecting a second amplitude of the optical pulse following passage through the sensor;
   II. placing a sample in the sample holding area;
   III. transmitting a pulsed THz radiation beam through a pixel area of the sample;
   IV. impinging the pulsed THz radiation beam following transmission through the sample onto the sensor while transmitting the optical probe beam through the sensor;
   V. detecting an amplitude of the probe beam emerging from the sensor;
   VI. repeating steps III–V a plurality of times to obtain a temporal profile of the THz pulse and calculate a frequency domain THz amplitude and frequency;
   VII. repeating steps III–VI a plurality of times for a plurality of sample pixel areas and for a plurality of sample orientations relative to the THz beam to obtain the composite frequency domain for a plurality of pixels from a plurality of angles; and
   VIII. reconstructing an image of the sample from the composite frequency domain.

14. The method according to claim 13 wherein the pulsed THz radiation beam is focused onto a sample in the sample holding area and the focusing system comprises a focusing element having a diameter smaller than a distance measured from the focusing element to the sample holding area.

15. The method according to claim 14 wherein the step of detecting an amplitude of the probe beam emerging from the sensor comprises optically detecting the amplitude changes in the probe beam.

16. The method according to claim 14 wherein the step of reconstructing an image of the sample comprises constructing at least one image representing a cross-sectional slice of the sample.

17. The method according to claim 14 wherein the image reconstructed is a 3D representation of the sample.

18. The method of claim 17 further comprising using a filtered back-projection algorithm to reconstruct the three-dimensional image.

19. The method of claim 14, wherein the step of detecting an amplitude of the probe beam emerging from the sensor comprises dynamic subtraction to improve the signal-to-noise ratio.

20. The method according to claim 19 wherein the pulsed THz radiation has a pulse rate and wherein the dynamic subtraction is performed using a detector comprising a CCD and a synchronization signal between the THz emitter and the CCD to regulate the scan frequency rate of the CCD relative to the THz pulse rate.

21. A method for performing computed tomography using THz-frequency radiation, the method comprising:
   I. obtaining a reference signal by:
      A. transmitting pulsed THz radiation through a path that includes a sample holding area and a focusing system and impinging the pulsed THz radiation onto a sensor, wherein the sample holding area is smaller than a Rayleigh range of a focused THz beam and the focusing system is designed to focus a plane adjacent the sample holding area onto the sensor,
      B. transmitting a chirped pulsed optical radiation probe beam having a first amplitude profile through the sensor when the sensor is illuminated with THz-frequency electromagnetic radiation, and
      C. detecting a second amplitude profile of the chirped optical pulse following passage through the sensor;
   II. placing a sample in the sample holding area;
   III. transmitting a pulsed THz radiation beam through a pixel area of the sample;
   IV. impinging the pulsed THz radiation beam following transmission through the sample onto the sensor while transmitting the optical probe beam through the sensor;
   V. detecting an amplitude as a function of frequency of the chirped probe beam emerging from the sensor and converting the amplitude as a function of frequency to an amplitude as a function of delay time thereby to obtain a temporal profile of the THz pulse;
   VI. calculating a frequency domain THz amplitude and frequency;
   VII. repeating steps III–VI a plurality of times for a plurality of sample pixel areas and for a plurality of sample orientations relative to the THz beam to obtain the composite frequency domain for a plurality of pixels from a plurality of angles; and
   VIII. reconstructing an image of the sample from the composite frequency domain.

22. The method according to claim 21 wherein the pulsed radiation beam is focused with the focusing system and the focusing system comprises a focusing element having a diameter smaller than a distance measured from the focusing element to the sample holding area.

23. The method according to claim 22 wherein the step of reconstructing an image of the sample comprises constructing at least one image representing a cross-sectional slice of the sample.

24. The method according to claim 22 wherein the image reconstructed is a 3D representation of the sample.

25. The method according to claim 21 wherein the step of detecting an amplitude as a function of frequency of the chirped probe beam emerging from the sensor comprises using a spectrometer and a CCD array.

* * * * *